US008195278B2

(12) United States Patent
Sun

(10) Patent No.: US 8,195,278 B2
(45) Date of Patent: Jun. 5, 2012

(54) METHOD FOR AUTOMATICALLY DETERMINING AN IMAGE PLANE HAVING A BIOPSY DEVICE THEREIN

(75) Inventor: Ying Sun, Singapore (SG)

(73) Assignee: Siemens Medical Solutions USA, Inc., Malvern, PA (US)

( * ) Notice: Subject to any disclaimer, the term of this patent is extended or adjusted under 35 U.S.C. 154(b) by 714 days.

(21) Appl. No.: 11/656,795

(22) Filed: Jan. 23, 2007

(65) Prior Publication Data
US 2007/0265525 A1 Nov. 15, 2007

Related U.S. Application Data

(60) Provisional application No. 60/800,339, filed on May 15, 2006.

(51) Int. Cl.
*A61B 5/05* (2006.01)
(52) U.S. Cl. ......... 600/427; 600/425; 382/128; 382/131
(58) Field of Classification Search .......... 600/410–424, 600/407, 427, 429; 382/128, 131, 184, 190, 382/209, 216, 291, 295
See application file for complete search history.

(56) References Cited

U.S. PATENT DOCUMENTS

| 6,529,766 | B1 | 3/2003 | Guendel | |
|---|---|---|---|---|
| 6,591,004 | B1* | 7/2003 | VanEssen et al. | 382/154 |
| 6,621,889 | B1* | 9/2003 | Mostafavi | 378/65 |
| 6,904,163 | B1* | 6/2005 | Fujimura et al. | 382/131 |
| 2004/0044279 | A1* | 3/2004 | Lewin et al. | 600/407 |
| 2004/0252870 | A1* | 12/2004 | Reeves et al. | 382/128 |
| 2005/0059879 | A1* | 3/2005 | Sutherland et al. | 600/411 |
| 2007/0161892 | A1* | 7/2007 | Eck et al. | 600/424 |

* cited by examiner

*Primary Examiner* — Brian Casler
*Assistant Examiner* — Rajeev Siripurapu
(74) *Attorney, Agent, or Firm* — Donald B. Paschburg

(57) ABSTRACT

A method for detection of the position and orientation of the tip of a needle-like medical device inserted into a tissue of a patient using scanning apparatus. The method obtains a first scan of the tissue correlating the needle-like medical device with a plurality of needle-like templates, each one having a different angular orientation to obtain an feature image of the device; obtains eigenvalues and an eigenvector of image to obtain the angular orientation of an image plane for a subsequent scan; transforms the orientation of the device in the determined image plane into scanning system reference coordinates with the longitudinal axis of the needle like device having a predetermined orientations with respect to the reference coordinate system; and makes observations along each of a sequence of lines transverse to the longitudinal axis of the image of the device in the determined plane to detect the tip of the device.

18 Claims, 8 Drawing Sheets

Image Volume

A Biopsy Device in an Image Volume

Orientation and Position of the Device in One Slice

Determination of a New Imaging Plane

METHOD FOR AUTOMATICALLY DETERMINING AN IMAGE PLANE HAVING A BIOPSY DEVICE THEREIN

CROSS REFERENCE TO RELATED APPLICATION

This application claims priority from U.S. Provisional application Ser. No. 60/800,339 filed on May 15, 2006 which is incorporated herein by reference.

TECHNICAL FIELD

This invention relates generally to medical imaging methods and more particularly to methods for automatically adjusting an image plane so that such image plane includes therein a needle-like device, such as a biopsy device, laparoscopes, etc. The invention is also related to a method for displaying the tip of a needle-like device situated in the body of a patient during a medical interventional procedure by means of an imaging modality method.

BACKGROUND AND SUMMARY

As is known in the art, medical imaging, such as MRI, CT and ultrasound have been used to detect a biopsy device that is inserted into tissue of a patient. More particularly, needle-like devices are introduced through the skin, through small orifices into the body of the patient during medical interventional procedures. The instruments are guided only according to "feel" or with the aid of an imaging diagnostic device, preferably with the aid of a tomography device or ultrasound.

In methods of the above type, the position of a slice of the body of the patient shown in a reconstructed image can be described, for example, by its position relative to the patient and its inclination relative to the longitudinal axis of the patient. These parameters should be selected such that the instrument, for example a puncture needle in a slice of the body of the patient shown in a tomogram, for example, can be guided to the desired object or site, for example to an organ of the patient. This task is difficult because: 1) the biopsy device is absent in most of the images; 2) the position and the orientation of the device may vary a lot among different studies; and 3) the signal strength at the device location can be very low.

One technique used to display the tip of a needle-like medical device is described in U.S. Pat. No. 6,529,766 entitled "Method for Displaying the Tip of a Medical Instrument Situated in the Body of a Patient, issued Mar. 4, 2003, inventor Lutz Guendel, assigned to the same assignees as the present invention. As described therein, the method displays the tip of a medical instrument situated in the body of a patient during a medical interventional procedure by means of an imaging method, including the steps of repeatedly acquiring data for a number of planar slices of the patient during the interventional procedure, subsequently analyzing the data to identify in which of the slices the tip of the instrument is situated, and generating a signal that marks the slice that contains the tip of the instrument. Only that slice that is identified by the signal produced by the tip of the instrument is reconstructed by means of the imaging method and is displayed at a display unit.

More particularly, as is known, each scan contains several slices that cover a volume. Among all the slices of one scan, the biopsy device is only present in typically at most three slices. Sometimes it only appears in a single slice. Therefore, the device may not appear in the first slice. When that happens, there is no way to obtain any useful information regarding the device based on the first slice. Thus, given a set of images of a number (5 to 11) of slices containing a biopsy device, the goal is to determine in which of the slices the biopsy device is situated and identify both the position and the orientation of the device in that slice. With this information, it is desired that the imaging plane of the next scan be automatically adjusted to be parallel to the biopsy device. Therefore, the biopsy needle and most importantly the tip of the needle can be clearly seen in the next scan.

In accordance with the present invention, a method is provided for detection of the position and orientation of the tip of a needle-like medical device inserted into a tissue of a patient using scanning apparatus, such method comprising: during an initial scan of the tissue with the apparatus, obtain several image slices through the tissue having therein the device, each one of the slices having a known orientation with respect to a reference co-ordinate system fixed with respect to the scanning apparatus; detecting the device in one of the slices obtained from the initial scan including identifying such one of the slices and the position and angular orientation of the device in such one of the slices; combining the identified one of the slices and the position and angular orientation of the device in such one of the slices with respect to the reference coordinate system of the scanning system to determine an appropriate imaging plane for a subsequent scan; repeating the process until a final slice is obtained having a predetermined degree of clarity of the entire needle-like device and with the needle-like device disposed in a known orientation with respect to the reference co-ordinate system; and identifying the tip of the device in the final slice.

In one embodiment, a method is provided for detection of the position and orientation of a needle-like medical device inserted into a tissue of a patient using scanning apparatus includes obtaining a first scan of the tissue correlating the needle-like medical device with a plurality of needle-like templates, each one of the templates having a different angular orientation to obtain an feature image of the device; thresholding the obtained feature image to obtain a binary image of the device; using connected component analysis (labeling) for candidate detection and using principal component analysis to obtain eigenvalues and eigenvectors of each candidate in the binary image; using the obtained eigenvalues and eigenvectors to detect the position and orientation of the device and therefore obtain the angular orientation of an image plane for a subsequent scan of the tissue.

In one embodiment, the method includes automatically determining the orientation of the image plane of the next scan having the device with a predetermined likelihood or greatest likelihood using the eigenvalues and the eigenvector associated with the largest eigenvalue obtained from a previous scan.

In one embodiment, position and orientation of the tip of the device is determined by a method comprising transforming the orientation of the device in the determined image plane into scanning system reference coordinates with the longitudinal axis of the needle like device having a predetermined orientations with respect to the reference coordinate system and making observations along each of a sequence of lines transverse to the longitudinal axis of the image of the device in the determined plane to detect the tip of the device.

In one embodiment, a method is provided for detection of the position and orientation a needle-like medical device inserted into a tissue of a patient using scanning apparatus. The method includes: obtaining in a first scan of the tissue, a plurality of slices of images having therein the medical device; for each one of the slices, determine eigenvalues and an eigenvector of an possible image of the device; and automatically determine the orientation of the image plane for a possible image of the medical device for a subsequent scan of the tissue using the eigenvector and eigenvalues of obtained from the first scan.

In one embodiment, the orientation of the image plane of the subsequent scan uses the eigenvalues of the first scan to determine the possible medical device images with a predetermined or greatest likelihood.

In one embodiment, a method is provided for detection of the position and orientation of the tip of a needle-like medical device inserted into a tissue of a patient using scanning apparatus. The method includes: obtaining in a first scan of the tissue, a plurality of slices of images having therein the medical device; for each one of the slices, determine eigenvalues and an eigenvector of an possible image of the device; automatically determine the orientation of the image plane for a possible image of the medical device for a subsequent scan of the tissue using the eigenvector and eigenvalues of obtained from the first scan; transforming the orientation of the image of the device in the subsequent scan into scanning system reference coordinates; and making observations along each of a plurality of lines transverse to the longitudinal axis of the image of the device in the scanning system reference system to detect the tip the device.

In one embodiment, a method is provided for detection of the position and orientation of the tip of a needle-like medical device inserted into a tissue of a patient using scanning apparatus. The method includes: obtaining a first scan of the tissue correlating the needle-like medical device with a plurality of needle-like templates, each one having a different angular orientation to obtain an feature image of the device; obtaining eigenvalues and an eigenvector of image to obtain the angular orientation of an image plane for a subsequent scan; transforms the orientation of the device in the determined image plane into scanning system reference coordinates with the longitudinal axis of the needle like device having a predetermined orientations with respect to the reference coordinate system; and making observations along each of a sequence of lines transverse to the longitudinal axis of the image of the device in the determined plane to detect the tip of the device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A showing a first one of the templates in a −45 degree rotation; FIG. 4B showing one of the templates in a zero degree rotation, and FIG. 4C showing one of the templates in a 45 degree rotation, such orientation being in the reference coordinate system of the scanning apparatus of FIG. 1.

Like reference symbols in the various drawings indicate like elements.

DETAILED DESCRIPTION

Figure 1:
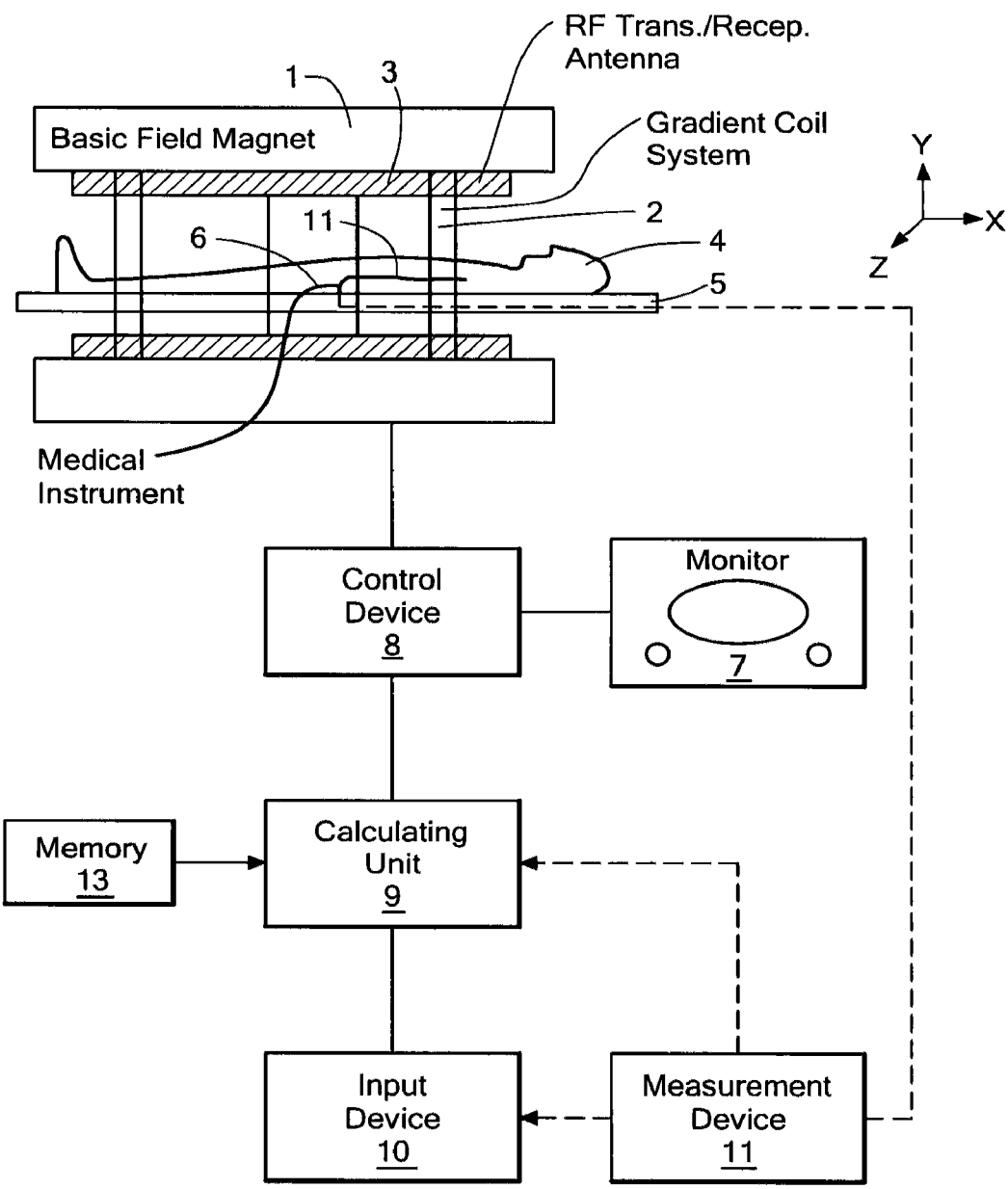
FIG. 1 is a schematic diagram of a magnetic resonance tomography apparatus having a program stored in a memory thereof for processing image data in accordance with the invention.

Referring now to FIG. 1 a section through a magnetic resonance tomography system or apparatus 10 is schematically shown that can be utilized for the implementation of the present method. Only the basic component parts of the apparatus 10 are shown in FIG. 1, namely a basic field magnet 1, a gradient coil system 2 and a radio-frequency transmission and reception antenna 3. A patient 4 also is shown on a patient bed 5, the patient 4 representing the examination subject. In the measurement, one or more radio-frequency pulses for generating magnetic resonance signals are radiated into the body of the person 4 via the radio-frequency transmission antenna 3, and the generated magnetic resonance signals are acquired and presented in the form of a two-dimensional MR tomogram or MIP image. With broken lines, FIG. 1 shows the body region 6 of the patient in which an introduced object, an elongated needle-like device 11 for example a biopsy device is shown inserted into tissue of the patient. Here the biopsy device 11 is inserted into the prostate gland of the patient and the method is used for detection of the position and orientation of the tip of the inserted biopsy device 11.

FIG. 1 also shows a control device 8 for operating the MR acquisition device for the implementation of an image acquisition as well as an image presentation device, a monitor 7 in the present case. Via an input device 10, usually in the form of a keyboard, as well as a multi-dimensional input device, for example a joystick, data are forwarded to a calculating unit 9 that implements the corresponding calculations and forwards the result to the control device 8. The system 10 includes a memory 13 for storing a computer program for enabling the apparatus to process image data in accordance with the method described herein. It is also noted that the system 10 has a reference X, Y, Z coordinate system, as shown in FIG. 1

As will be described in more detail below the apparatus 10 shown in FIG. 1 is used to obtain a set of images of 5 to 11 slices containing the biopsy device 11, the goal is to determine both the position and the orientation of the device 11. With this information, it is desired that the imaging plane of the next scan be automatically adjusted to be parallel to the biopsy device. Therefore, the biopsy needle and most importantly the tip of the needle can be clearly seen in the next scan.

Figure 2:
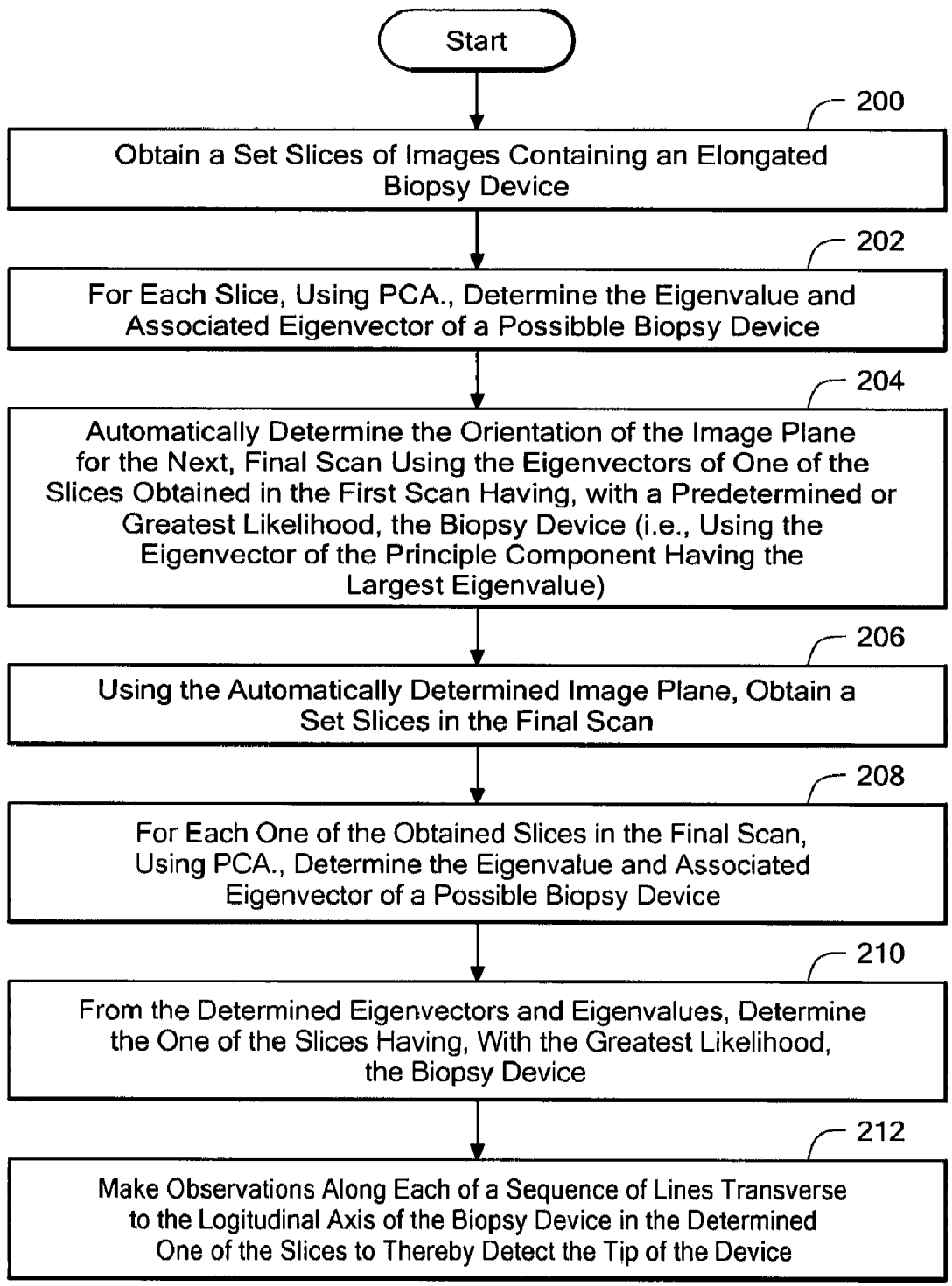
FIG. 2 is a flow diagram of the method according to the invention used to first determine the position and orientation of an elongated needle-like medical device inserted into a tissue of a patient using scanning apparatus, then automatically align an image of the device with respect to the reference coordinate system of the scanning apparatus if FIG. 1, and then determine the tip of the device.

Referring now to FIG. 2, a flow diagram is shown of the method used to first determine the position and orientation of an elongated needle-like medical device inserted into a tissue of a patient using scanning apparatus, then automatically align an image of the device with respect to a reference coordinate system of the scanning apparatus, and then determine the tip of the device. Briefly, the method, during an initial scan of the tissue with the apparatus, obtains several image slices through the tissue having therein the device, each one of the slices having a known orientation with respect to a reference co-ordinate system fixed with respect to the scanning apparatus, Step 200. Next, the method detects the device in one of the slices obtained from the initial scan including determining the position and angular orientation of the device in such one of the slices, Step 202. Next, the method references the position and angular orientation of the device in such one of the slices with respect to the reference coordinate system of the scanning system to determine an appropriate imaging plane for a subsequent scan, Step 204. The process is repeated until a final slice is obtained having a predetermined degree of clarity of the entire needle-like device and with the longitudinal axis of the needle-like device disposed in a known orientation with respect to the reference co-ordinate system. More particularly, using the automatically determined image plane, obtain a set of slices in the final scan. Step 206. For each one of the obtained slices in the final scan, using PCA, determine the eigenvalue and associated eigenvector of a possible biopsy device, Step 208. From the determined eigenvector and eigenvalue, determine the one of the slices in the final scan having, with greatest likelihood, the biopsy device, Step 210. Reference is made to FIGS. 2B through 2E which shows the sequence of determining, from the determined eigenvector (FIG. 2D), the new or final image plane (FIG. 2E).

It is understood that the eigenvector of the image is the first principal eigenvector of the covariance matrix of the coordinates of the pixels belonging to the detected component that corresponds to the device. Finally, the tip of the device is identified in the final slice comprising obtaining data along lines transverse to the longitudinal axis of the device, Step 212.

Figure 3:
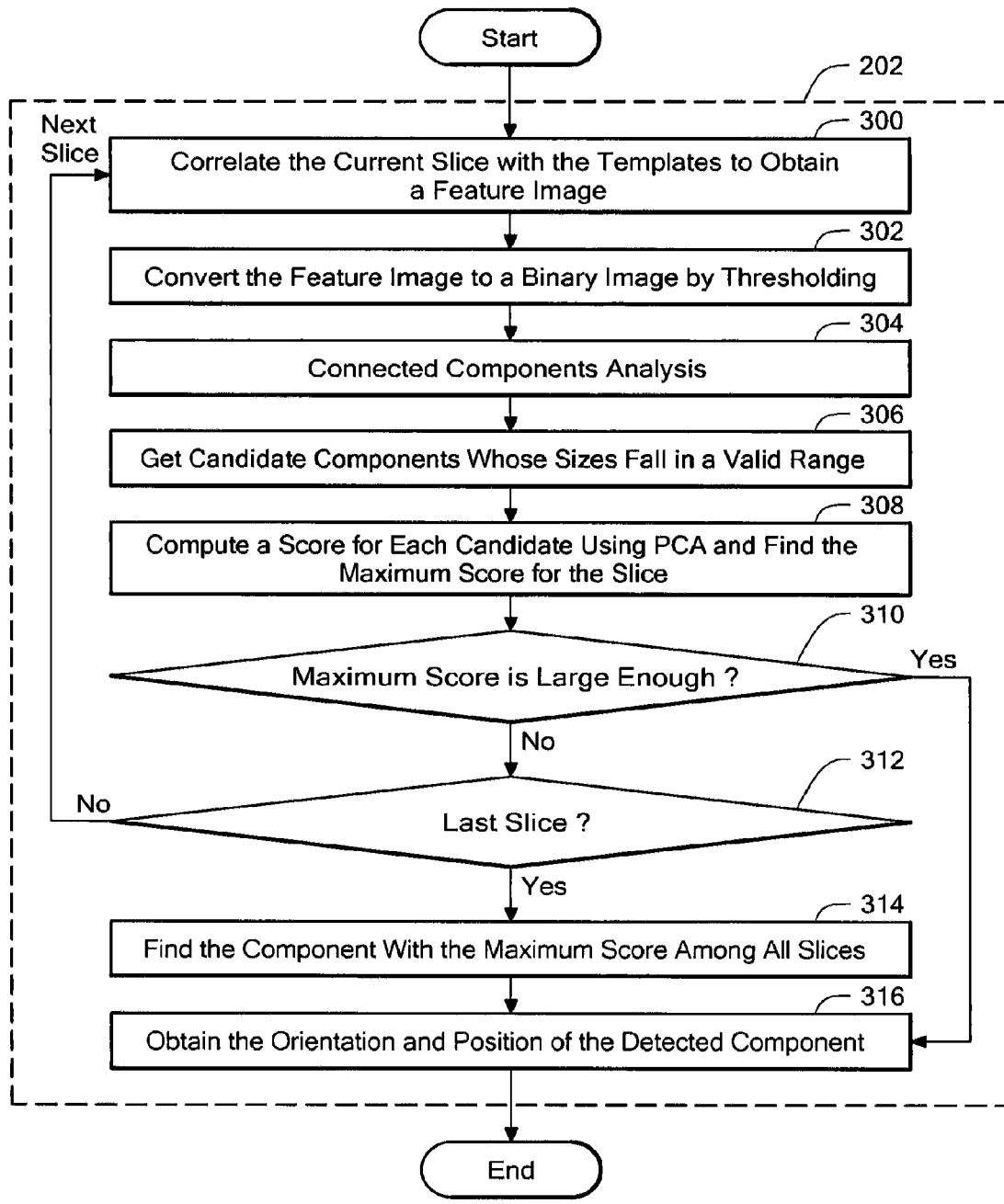
FIG. 3 is a flow diagram of the process used to determine the image plane having the device image therein and used to detect the tip on the device in accordance with the invention.
Figure 4A:
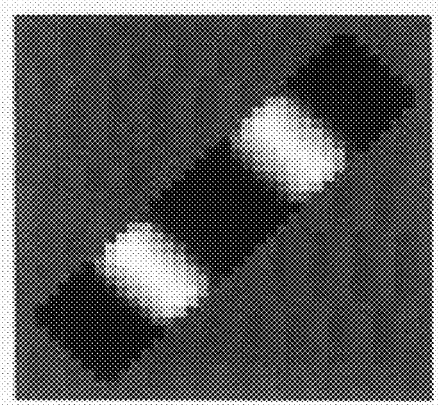
FIGS. 4A-4C are three normalized 2-D templates for the biopsy device.
Figure 4B:
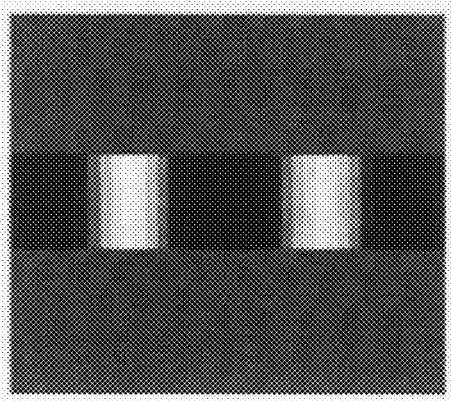
Figure 4C:
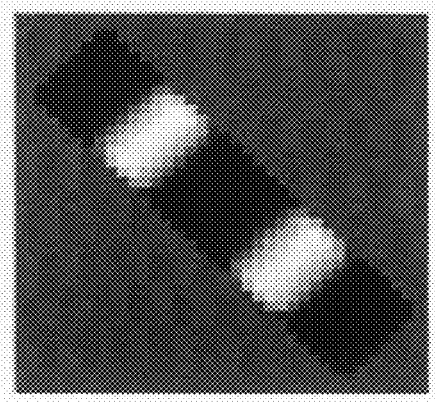

Referring now to FIG. 3, a flow diagram is shown of the process used to determine the final slice; i.e., details of Step 202 in FIG. 2. It is first noted that because the physical dimension and appearance of the biopsy device (tube) is fixed and known, (i.e., the device is an elongated, needle-like device) a template bank is constructed that captures this distinct feature of the device and localizes the device using rotation-invariant template matching. Here, three, two-dimensional (2-D) elongated templates shown in FIGS. 4A-4C are obtained with orientations at −45 degree, zeros degree, and 45 degree, respectively, as shown, in the reference system coordinates.

Figure 2A:
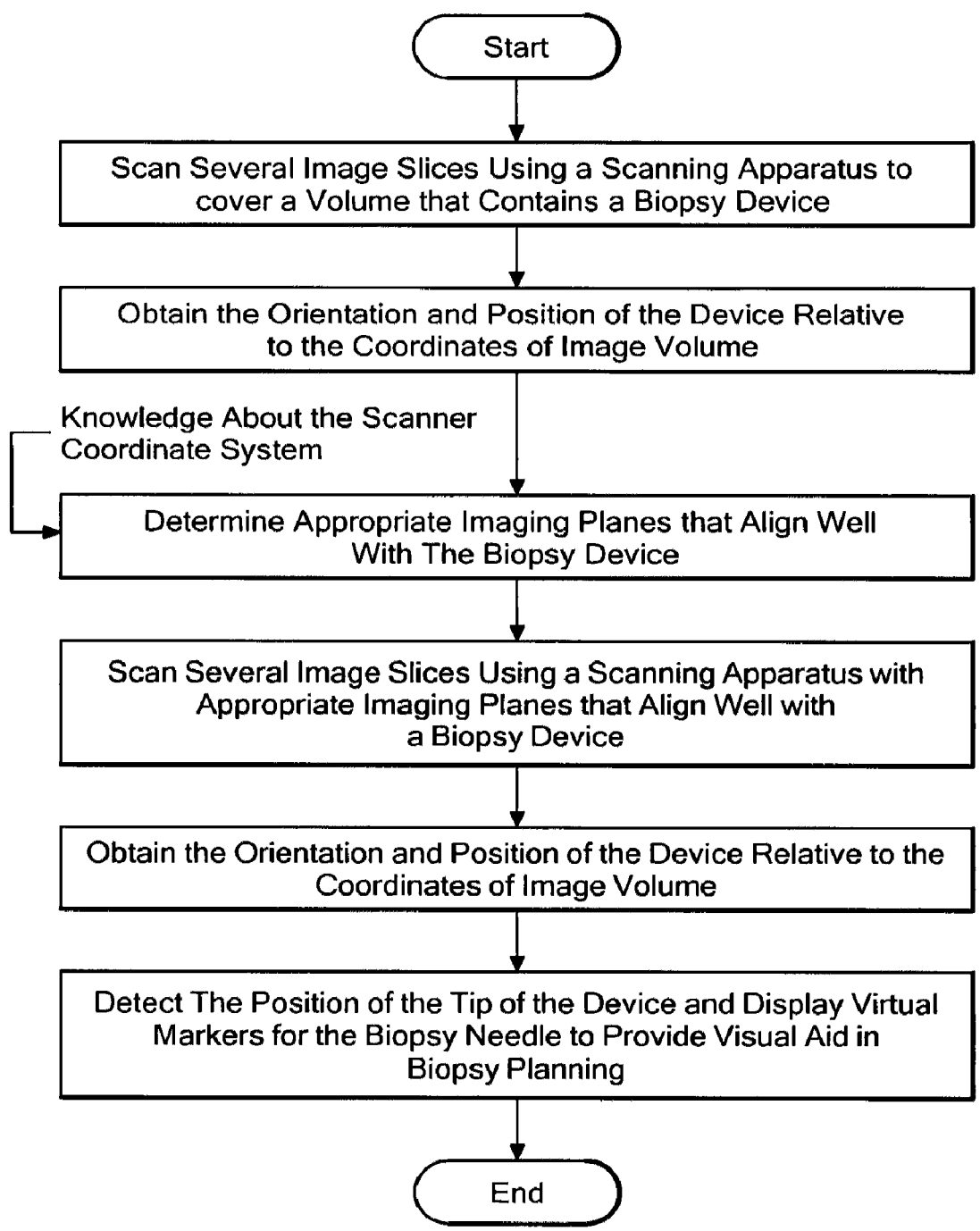
FIG. 2A is more detailed flow diagram of the flow diagram of FIG. 2.
Figure 2B:
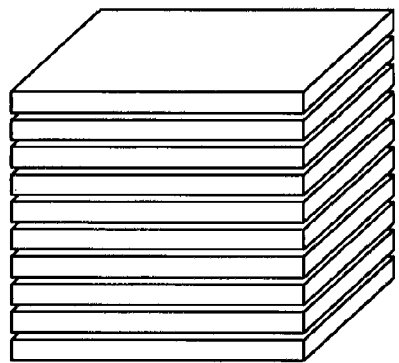
FIGS. 2B through 2E shows the sequence of determining a new or final image plane in accordance with the invention.
Figure 2C:
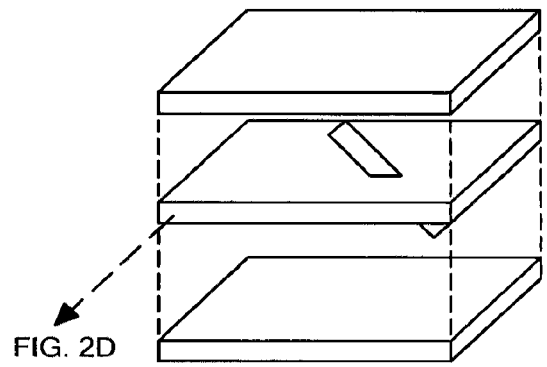
Figure 2D:
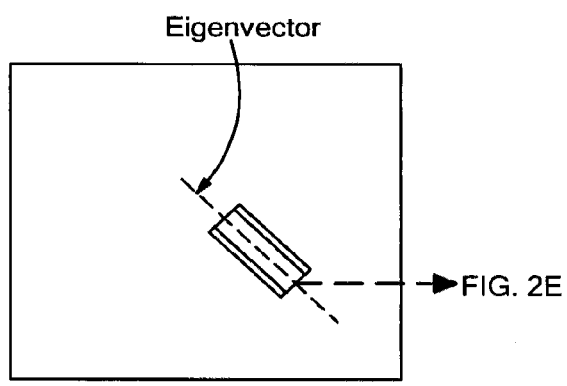
Figure 2E:
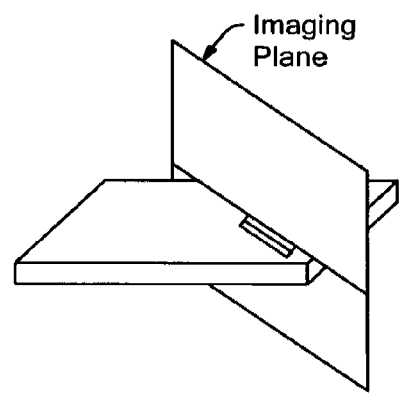

To put it another way, the process described above in connection with FIG. 2 is shown in the flow diagram of FIG. 2A. The process scans several image slices using a scanning apparatus to cover a volume that contains a biopsy. Next, the process obtains the orientation and position of the device relative to the coordinates of image volume. Next, the process determines appropriate imaging planes that align well with the biopsy device using knowledge about the scanner coordinate system. Next, the process scans several image slices using a scanning apparatus with appropriate imaging planes that align well with a biopsy device. Next, the process obtains the orientation and position of the device relative to the coordinates of image volume. Finally, the process detects the position of the tip of the device and display virtual markers for the biopsy needle to provide visual aid in biopsy planning Referring again to FIG. 3, (i.e., the details of Step 202 in FIG. 2) the process first obtains the feature image by normalized cross correlation between the template and the device 11 (Step 300). Let $c_k(x,y)$ denote the correlation coefficient between the current slice and the k th template at pixel position (x,y), k=1, 2, 3. The value of the feature image f at pixel (x,y) is given by $$f(x,y) = \max\{c_k(x,y)\}. \tag{1}$$

The correlation coefficient $c_k(x,y)$ is computed by $$c_k(x, y) = \frac{\sum_{u,v} [f(u, v) - \bar{f}(x, y)][t_k(u - x, v - y) - \bar{t}_k]}{\sqrt{\sum_{u,v} [f(u, v) - \bar{f}(x, y)]^2 \sum_{u,v} [t_k(u - x, v - y) - \bar{t}_k]^2}}, \tag{2}$$

where $\bar{t}_k$ is the mean of the k th template and $\bar{f}(x,y)$ is the mean of f in the region under the template. By using the cosine-like correlation coefficient that normalizes the image and feature vectors to unit length, the feature image overcomes the difficulties caused by changes in image amplitude. By taking the maximum correlation coefficient resulting from all the templates, the feature image is invariant to the allowable rotation of the device.

Next, a binary image is obtained by thresholding the feature image, Step 302. In the binary image, a biopsy device 11 corresponds to a single line segment. In order to identify the biopsy device 11, first, connected component analysis, sometimes also referred to as connected component labeling, is performed on the binary image, Step 304. Connected components analysis is used to identify isolated regions in the binary image; these isolated regions are considered as candidates for possible device detection. Connected components labeling scans an image and groups its pixels into components based on pixel connectivity. The process extracts and labels various disjoint and connected components in an image. Each disjoint and connected component is considered as a candidate for detecting the device. It should be understood that region growing can be used in place of connected components labeling.

Then, the size of each connected component is calculated; only those components whose region sizes fall in a valid range are kept as candidates, Step 306. Finally, principal components analysis (PCA) is performed to obtain the eigenvalues and the eigenvectors of each candidate, Step 308.

Let $\lambda_1$ and $\lambda_2$, $\lambda_1 > \lambda_2 > 0$, denote two eigenvalues of one candidate. Let A denote the area of the candidate, we introduce a score, $$s = \frac{\lambda_1}{\lambda_2} A,$$

to measure how much the candidate region resembles the biopsy device.

Next, the method selects from among all the candidates for the current slice, the largest score, s, as "winner of the slice", Step 310 through Steps 314. More particularly, if the largest score is greater than a pre-defined threshold, the "winner of the slice" is declared as "winner of the volume", and the process jumps to the next step, Step 316 (to be described); otherwise Steps 302 through 308 are repeated for the next slice until the last slice of the volume is processed. The process goes from slice to slice in MR by adjusting the position of the imaging plane along the slice selection axis.

If "winner of the volume" has not been declared after the last slice is processed, the algorithm declares the candidate with the maximum score among all the slices as "winner of the volume". Step 314 and continues with the next step, Step 316. The "winner of the volume" has been referred to above as the "final slice". Thus, in Step 314, the process finds the component with the maximums score, s, from among all the slices.

Next, in Step 316, an estimation of the device position and orientation are obtained by relative to the reference coordinates of the image volume, by computing respectively from the "final slice" (i.e., "winner of the volume") the center of mass of the winning component and the orientation of its largest principal component. (Note that the co-ordinates of the center of mass is the average of the co-ordinates of non-zero pixels that belong to the detected component in the binary image). This completes Step 202 in FIG. 2.

The process then combines the identified one of the slices and the position and angular orientation of the device in such one of the slices with respect to the reference coordinate system of the scanning system to determine an appropriate imaging plane for a subsequent scan; repeating the process until a final slice is obtained having a predetermined degree of clarity of the entire needle-like device and with the needle-like device disposed in a known orientation with respect to the reference co-ordinate system; and identifying the tip of the device in the final slice. It should be noted that the rotation angle is computed automatically. It is the angle determined by the eigenvector of the principal component with the larger eigenvalue.

Having now determined the position and orientation of an elongated needle-like medical device inserted into a tissue of a patient using scanning apparatus, then automatically align an image of the device with respect to a reference coordinate system of the scanning apparatus until a final slice is obtained having a predetermined degree of clarity of the entire needle-like device and with the longitudinal axis of the needle-like device disposed in a known orientation with respect to the reference co-ordinate system, the process now determines the tip of the device. For example, here the process rotates the image to appear in the predetermined orientation, here in a vertical orientation in the reference coordinate system, as shown for a biopsy device inserted into the prostate gland of a patient in FIG. 5. The process then places a mark on the image of the detected tip and also places equidistant length markers on the image to be able to better judge the positioning of the device.

More particularly, in the first step, the position and the orientation of the biopsy device 11 are determined using the auto-align algorithm described above. Let I denote the selected slice. Let $(c_x, c_y)$ and $\theta$ denote the position and the orientation, respectively, in the selected slice. A new image I' is generated by $$I' = R(\theta; c_x, c_y) I, \quad (1)$$

where $R(\theta; c_x, c_y)$ denotes a rotation by $\theta$ centered at $(c_x, c_y)$. FIG. 1 displays two reoriented TSE MR images. As shown, the tube has been re-oriented to its vertical orientation in these images.

Figure 5:
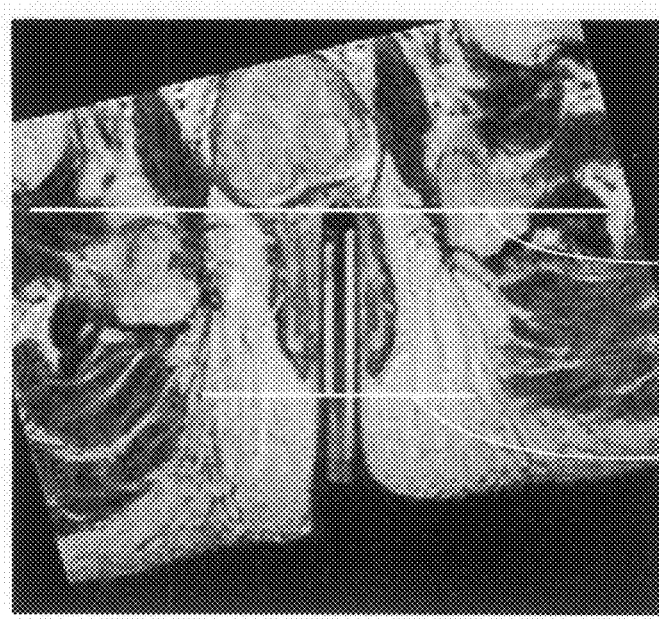
FIG. 5 is an image of a biopsy medical device inserted into the prostate gland of a patient, such device being orientated in a predetermined, here vertical orientation in accordance with the invention.
Figure 6A:
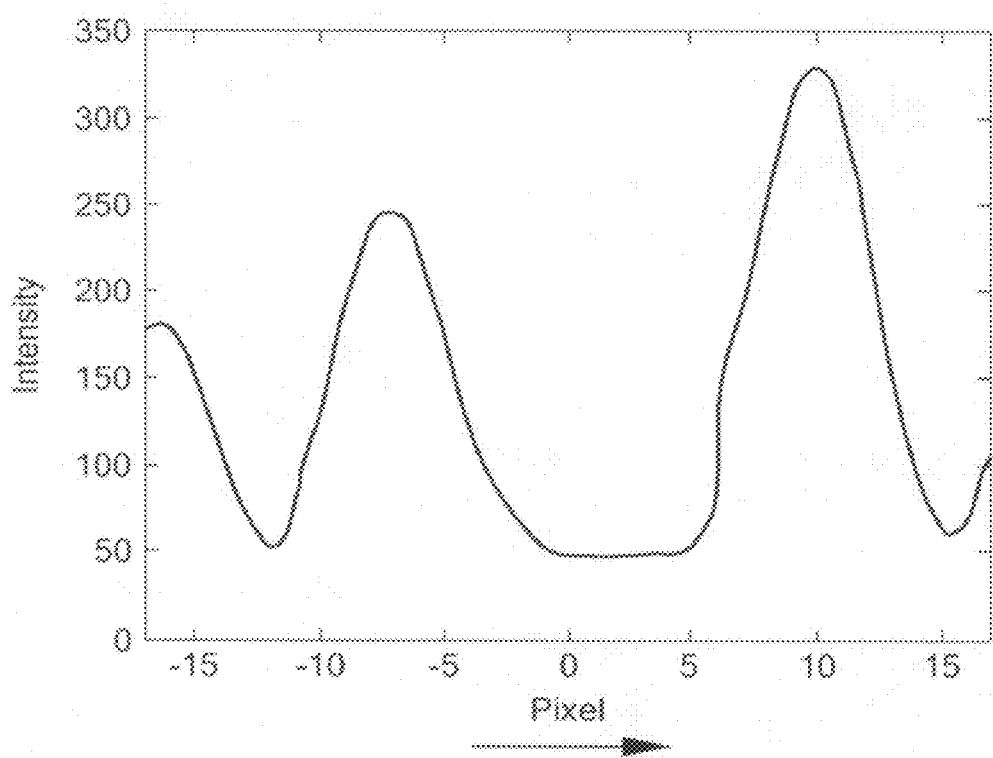
FIG. 6A is plot of a 1-D reference profile estimated along a line transverse to the longitudinal axis of the biopsy device at the center of the biopsy device, such reference profile is data-specific, here transversal orientation in accordance with the invention.

Next the tip of the device is detected. More particularly, process includes: transforming the orientation of the device in the determined image plane into scanning system reference coordinates with the longitudinal axis of the needle like device having a predetermined orientations with respect to the reference coordinate system; and making observations along each of a sequence of lines transverse to the longitudinal axis of the image of the device in the determined plane to detect the tip of the device. Here the predetermined orientation of the longitudinal axis of the device is vertical as shown in FIG. 5. Here, an exemplary one of the lines, here shown as a line 400 in FIG. 6, is disposed along the y axis of the coordinate system of the image volume. The observation along line 400, the observation along the Y axis is the correlation coefficient, $C(\Delta y)$, between the sampled 1-D profile for each transversal line (i.e., line 400) with the reference 1-D profile estimated at the center of the device (i.e., the profile shown in FIG. 6A).

Figure 6B:
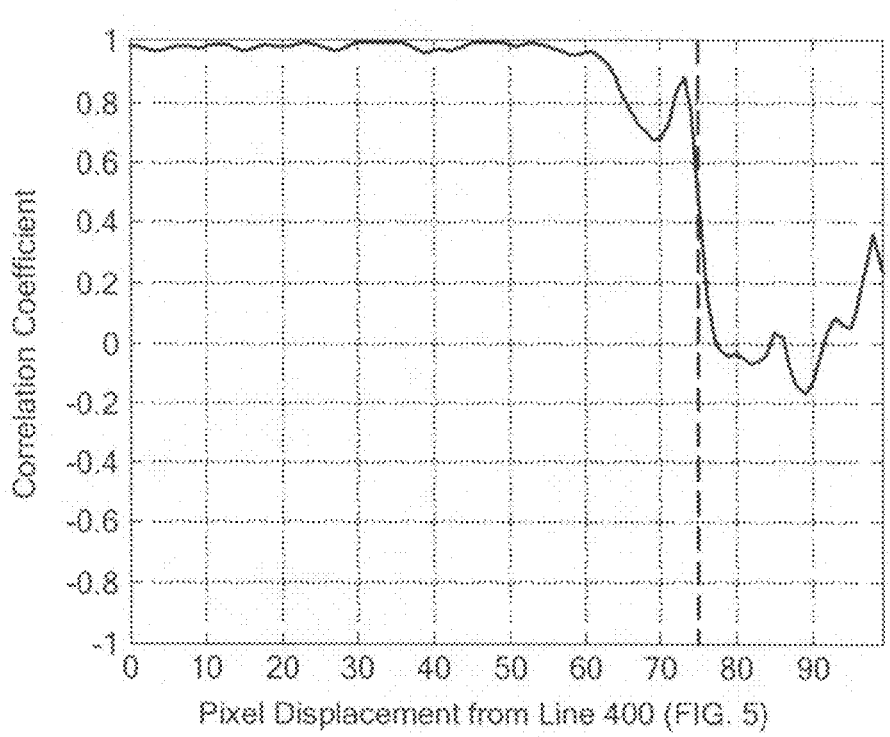
FIG. 6B is plot of resulting correlation coefficients along the longitudinal axis of a needle-like device, such correlation coefficient being between a 1-D reference profile and the 1-D profile sampled along each of a sequence of lines transverse to the longitudinal axis of the image of the device in the determined plane to detect the tip of such device, here longitudinal axis in accordance with the invention.

More particularly, after re-orientation, a horizontal 1-D reference profile is estimated at the center of the tube. Unlike the 2-D templates for the device, this 1-D profile is data-specific. One example is shown in FIG. 6A. Starting from the center of the tube, the correlation coefficient, $C(\Delta y)$ as a function of the current 1-D profile, i.e., along the Y axis, and the reference 1-D profile is computed along the vertical direction, as a function of vertical offset (i.e., a sequence of lines along the longitudinal axis, here the X axis, of the device, from the center: $C(\Delta y)$. FIG. 6A is a plot of pixel intensity for the image shown in FIG. 5 as a function of distance in pixels to the center of the device along the horizontal axis, (i.e., the axis transverse to the longitudinal axis of the device, i.e., along line 400 in FIG. 5). The tip is identified by searching for the smallest $\Delta y^*$ that satisfies the following two conditions:
(a) $C(\Delta y)$ experiences a significant drop at $\Delta y^*$, $$\text{i.e., } C(\Delta y^*) > 0.5 \text{ and } \frac{C(\Delta y^*) - C(\Delta y^* + 1)}{C(\Delta y^*)} > 0.3 \text{ or } C(\Delta y^* + 1) < 0.3;$$

and (b) the value of C(dy) stays small, i.e., $\forall$ dy, $1 \leq dy \leq K$, $C(\Delta y^* + dy) < 0.8$, where K is the maximum gap allowed between two consecutive tube segments. In FIG. 5B, the offset $\Delta y^*$ that corresponds to the tip position is indicated by the vertical line 500. Thus, FIG. 6B shows the relationship between correlation coefficient and a pixel location indicated displaced from the line 400. Thus, as shown in FIG. 6B there is a significant lack of correlation starting at 75 pixels (i.e., the correlation coefficient is about 0.4) from the line 400 indicating that the tip is 75 pixels up from the center of the device, i.e., along line 400' in FIG. 6B. A second feature is also observed to detect that the tip is in, this example, 75 pixels from the center of the device (i.e., the correlation coefficient remains relatively low and does not increase significantly as the pixel locations increase from the center thereby insuring that the tip is not being confused with any gel that may be near the tip.

Finally, the tip 502 is identified by mapping the point specified by $\Delta y^*$ back to the coordinates of the original image as shown in FIG. 5.

Thus, the process may be summarized as: during an initial scan of the tissue with the apparatus, obtain several image slices through the tissue having therein the device, each one of the slices having a known orientation with respect to a reference co-ordinate system fixed with respect to the scanning apparatus; detecting the device in one of the slices obtained from the initial scan including determining the position and angular orientation of the device in such one of the slices; referencing the position and angular orientation of the device in such one of the slices with respect to the reference coordinate system of the scanning system to determine an appropriate imaging plane for a subsequent scan; repeating the process until a final slice is obtained having a predetermined degree of clarity of the entire needle-like device and with the longitudinal axis of the needle-like device disposed in a known orientation with respect to the reference co-ordinate system; and identifying the tip of the device in the final slice comprising obtaining data along lines transverse to the longitudinal axis of the device. More particularly, the process includes: obtaining a first scan of the tissue correlating the needle-like medical device with a plurality of needle-like templates, each one of the templates having a different angular orientation to obtain an feature image of the device; thresholding the obtained feature image to obtain a binary image of the device; using connected component analysis (labeling) for candidate detection and using principal component analysis to obtain eigenvalues and eigenvectors of each candidate in the binary image; using the obtained eigenvalues and eigenvectors to detect the position and orientation of the device and therefore obtain the angular orientation of an image plane for a subsequent scan of the tissue. Still more particularly, the process includes: using component analysis and labeling to obtain eigenvalues and an eigenvector of the binary image to obtain the angular orientation of an image plane for a subsequent scan of the tissue comprising automatically determining the orientation of the image plane of the next scan having the device with a predetermined likelihood or greatest likelihood using the eigenvalues and eigenvector obtained from the first scan.

Next the tip of the device is detected. More particularly, the process includes: transforming the orientation of the device in the determined image plane into scanning system reference coordinates with the longitudinal axis of the needle like device having a predetermined orientations with respect to the reference coordinate system; and making observations along each of a sequence of lines transverse to the longitudinal axis of the image of the device in the determined plane to detect the tip of the device.

Figure 7:
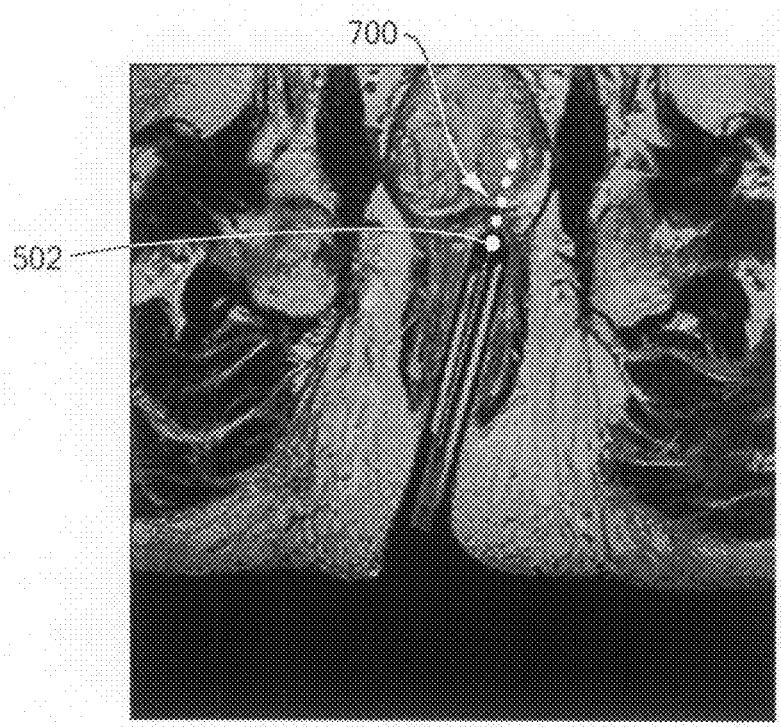
FIG. 7 is the image of the biopsy medical device with the tip thereof being detected in accordance with the invention and where evenly spaced markers are displayed on top of the original images as a targeting aid.

FIG. 7 is the image of the biopsy medical device with the tip thereof being detected in accordance with the invention and where evenly spaced markers 700 are displayed on top of the original images as a targeting aid.

A number of embodiments of the invention have been described. Nevertheless, it will be understood that various modifications may be made without departing from the spirit and scope of the invention. For example, instead of using principal component analysis (PCA), an alternative technique is to fit a 2-D line to the coordinates of pixels that belong to each candidate. The process can use the ratio between the projected length on the line and the average distance to the line to substitute for the ratio between the eigenvalue of the first principal component and the eigenvalue of the second principal component. The orientation of the line should correspond to the eigenvector of the first principal component. Accordingly, other embodiments are within the scope of the following claims.

What is claimed is:

1. A method for detecting the position and orientation of a tip of an elongated needle-like medical device inserted into tissue of a patient using a scanning apparatus, said method comprising the steps of: obtaining a plurality of image slices through the tissue having therein the device during a first scan of the tissue using the scanning apparatus, each image slice having a known orientation with respect to a reference co-ordinate system of the scanning apparatus, the plurality of image slices forming a first image volume;

determining a position and angular orientation of the device relative to coordinates of the first image volume in each slice obtained from the first scan;

determining an appropriate imaging plane for a subsequent scan by referencing the position and angular orientation of the device in each said slice to the reference coordinate system of the scanning apparatus, wherein a longitudinal axis of the device is aligned in an imaging plane of known orientation with respect to the reference coordinate system;

obtaining a plurality of image slices through the tissue having therein the device during a subsequent scan of the tissue with the apparatus with said imaging planes aligned with said longitudinal axis of said device, the plurality of image slices forming a subsequent image volume;

determining the orientation and position of the device relative to the coordinates of the subsequent image volume from the image slices of the subsequent scan; identifying the tip of the device in a final slice from pixel intensities sampled along the longitudinal axis of the device;

wherein determining a position and angular orientation of the device in a slice comprises: calculating a feature image from a normalized cross correlation of the slice with a plurality of device templates, each template having a different angular orientation;

thresholding the feature image to obtain a binary image of the device;

identifying connected regions in the binary image as candidate device regions;

calculating a score for each candidate device region from an area of each region and a ratio of its largest and smallest eigenvalues, and selecting a candidate device region with a highest score as representing the device; and estimating the position and orientation of the device from a center of mass of the selected candidate device region and from the orientation of a largest eigenvector of the candidate device region.

2. The method of claim 1, wherein identifying connected regions comprises using connected component analysis to identify isolated regions in the binary image,
selecting connected regions whose area falls within a pre-selected range; and
calculating eigenvectors and eigenvalues of each selected connected region using principle component analysis.

3. The method of claim 2, wherein the orientation and position of the device relative to the coordinates of image volume from the image slices of the subsequent scan are determined using said eigenvectors and eigenvalues calculated from the connected region obtained from the image slices of said first scan.

4. The method of claim 1, wherein determining the orientation and position of the device relative to the coordinates of image volume from the image slices of the subsequent scan further comprises determining eigenvectors and associated eigenvalues of a candidate device in each image slice of the subsequent scan using principle component analysis, and selecting the final slice as the slice with a greatest likelihood of representing the device.

5. The method of claim 1, wherein identifying the tip of the device in a final slice comprises:
rotating the final image into a predetermined orientation in the reference coordinate system;
estimating a reference profile along a center of the device in the rotated final image;
selecting a reference position along the reference profile;

calculating a correlation coefficient as a function of pixel intensities sampled at various offsets along the reference profile from the reference position and a pixel intensity sampled at the reference position; and identifying the tip from a smallest offset from the reference position whose correlation coefficient decreases in value and does not increase for increased offsets.

6. A method for detecting the position and orientation of a tip of an elongated needle-like medical device inserted into tissue of a patient using a scanning apparatus, said method comprising the steps of obtaining a plurality of image slices through the tissue having therein the device during a first scan of the tissue using the scanning apparatus, each image slice having a known orientation with respect to a reference co-ordinate system of the scanning apparatus;

calculating a feature image from a normalized cross correlation of each slice with a plurality of device templates, each template having a different angular orientation;

thresholding each feature image to obtain a binary image of the device;

identifying connected regions in each binary image as candidate device regions;

calculating a score for each candidate device region from an area of each region and a ratio of its largest and smallest eigenvalues, and selecting a candidate device region with a highest score as representing the device; and estimating the position and orientation of the device from a center of mass of the selected candidate device region and from the orientation of a largest eigenvector of the candidate device region.

7. The method of claim 6, further comprising:

determining an appropriate imaging plane for a subsequent scan by referencing the position and angular orientation of the device to the reference coordinate system of the scanning apparatus, wherein a longitudinal axis of the device is aligned in an imaging plane of known orientation with respect to the reference co-ordinate system;

obtaining a plurality of image slices through the tissue having therein the device during a subsequent scan of the tissue with the apparatus with said imaging planes aligned with said longitudinal axis of said device;

determining the orientation and position of the device relative to the coordinates of the image slices from the image slices of the subsequent scan; and identifying the tip of the device in a final slice from pixel intensity samples obtained along the longitudinal axis of the device.

8. A method for detecting the position and orientation of a tip of an elongated needle-like medical device inserted into tissue of a patient using a scanning apparatus, said method comprising the steps of:

obtaining a plurality of image slices through the tissue having therein the device during a scan of the tissue using the apparatus with imaging planes aligned with a longitudinal axis of said device;

determining the orientation and position of the device relative to the coordinates of the image slices from the image slices of the scan by determining eigenvectors and associated eigenvalues of a candidate device in each image slice of the subsequent scan using principle component analysis, and selecting a final slice as the slice with a greatest likelihood of representing the device;

rotating the final image into a predetermined orientation in the reference coordinate system;

estimating a reference profile along a center of the device in the rotated final image;

selecting a reference position along the reference profile;

calculating a correlation coefficient as a function of pixel intensities sampled at various offsets along the reference profile from the reference position and a pixel intensity sampled at the reference position; and identifying the tip from a smallest offset from the reference position whose correlation coefficient decreases in value and does not increase for increased offsets.

9. The method of claim 8, before obtaining a plurality of image slices through the tissue having therein the device during a scan of the tissue with the apparatus with imaging planes aligned with a longitudinal axis of said device, comprising:

obtaining a plurality of image slices through the tissue having therein the device during a first scan of the tissue with the scanning apparatus, each image slice having a known orientation with respect to a reference co-ordinate system of the scanning apparatus, the plurality of image slices forming a first image volume;

calculating a feature image from a normalized cross correlation of the slice with a plurality of device templates, each template having a different angular orientation;

thresholding the feature image to obtain a binary image of the device; identifying connected regions in the binary image as candidate device regions; calculating a score for each candidate device region from an area of each region and a ratio of its largest and smallest eigenvalues, and selecting a candidate device region with a highest score as representing the device;

estimating the position and orientation of the device from a center of mass of the selected candidate device region and from the orientation of a largest eigenvector of the candidate device region; and determining an appropriate imaging plane for the scan by referencing the position and angular orientation of the device in each said slice to the reference coordinate system of the scanning apparatus, wherein a longitudinal axis of the device is aligned in an imaging plane of known orientation with respect to the reference coordinate system.

10. A program storage device readable by a computer, tangibly embodying a program of instructions executable by the computer to perform the method steps for detecting the position and orientation of a tip of an elongated needle-like medical device inserted into tissue of a patient using a scanning apparatus, said method comprising the steps of:

obtaining a plurality of image slices through the tissue having therein the device during a first scan of the tissue using the scanning apparatus, each image slice having a known orientation with respect to a reference co-ordinate system of the scanning apparatus, the plurality of image slices forming a first image volume;

determining a position and angular orientation of the device relative to coordinates of the first image volume in each slice obtained from the first scan;

determining an appropriate imaging plane for a subsequent scan by referencing the position and angular orientation of the device in each said slice to the reference coordinate system of the scanning apparatus, wherein a longitudinal axis of the device is aligned in an imaging plane of known orientation with respect to the reference coordinate system;

obtaining a plurality of image slices through the tissue having therein the device during a subsequent scan of the tissue with the apparatus with said imaging planes aligned with said longitudinal axis of said device, the plurality of image slices forming a subsequent image volume;

determining the orientation and position of the device relative to the coordinates of the subsequent image volume from the image slices of the subsequent scan;

identifying the tip of the device in a final slice from pixel intensities sampled along the longitudinal axis of the device;

wherein determining a position and angular orientation of the device in a slice comprises: calculating a feature image from a normalized cross correlation of the slice with a plurality of device templates, each template having a different angular orientation;

thresholding the feature image to obtain a binary image of the device; identifying connected regions in the binary image as candidate device regions;

calculating a score for each candidate device region from an area of each region and a ratio of its largest and smallest eigenvalues, and selecting a candidate device region with a highest score as representing the device; and estimating the position and orientation of the device from a center of mass of the selected candidate device region and from the orientation of a largest eigenvector of the candidate device region.

11. The computer readable program storage device of claim 10, wherein identifying connected regions comprises using connected component analysis to identify isolated regions in the binary image,
   selecting connected regions whose area falls within a preselected range; and
   calculating eigenvectors and eigenvalues of each selected connected region using principle component analysis.

12. The computer readable program storage device of claim 11, wherein the orientation and position of the device relative to the coordinates of image volume from the image slices of the subsequent scan are determined using said eigenvectors and eigenvalues calculated from the connected region obtained from the image slices of said first scan.

13. The computer readable program storage device of claim 10, wherein determining the orientation and position of the device relative to the coordinates of image volume from the image slices of the subsequent scan further comprises determining eigenvectors and associated eigenvalues of a candidate device in each image slice of the subsequent scan using principle component analysis, and selecting the final slice as the slice with a greatest likelihood of representing the device.

14. The computer readable program storage device of claim 10, wherein identifying the tip of the device in a final slice comprises:
   rotating the final image into a predetermined orientation in the reference coordinate system;
   estimating a reference profile along a center of the device in the rotated final image;
   selecting a reference position along the reference profile;
   calculating a correlation coefficient as a function of pixel intensities sampled at various offsets along the reference profile from the reference position and a pixel intensity sampled at the reference position; and
   identifying the tip from a smallest offset from the reference position whose correlation coefficient decreases in value and does not increase for increased offsets.

15. A program storage device readable by a computer, tangibly embodying a program of instructions executable by the computer to perform the method steps for detecting the position and orientation of a tip of an elongated needle-like medical device inserted into tissue of a patient using a scanning apparatus, said method comprising the steps of
   obtaining a plurality of image slices through the tissue having therein the device during a first scan of the tissue using the scanning apparatus, each image slice having a known orientation with respect to a reference co-ordinate system of the scanning apparatus;
   calculating a feature image from a normalized cross correlation of each slice with a plurality of device templates, each template having a different angular orientation;
   thresholding each feature image to obtain a binary image of the device; identifying connected regions in each binary image as candidate device regions; calculating a score for each candidate device region from an area of each region and a ratio of its largest and smallest eigenvalues, and selecting a candidate device region with a highest score as representing the device; and
   estimating the position and orientation of the device from a center of mass of the selected candidate device region and from the orientation of a largest eigenvector of the candidate device region.

16. The computer readable program storage device of claim 15, the method further comprising:
   determining an appropriate imaging plane for a subsequent scan by referencing the position and angular orientation of the device to the reference coordinate system of the scanning apparatus, wherein a longitudinal axis of the device is aligned in an imaging plane of known orientation with respect to the reference co-ordinate system;
   obtaining a plurality of image slices through the tissue having therein the device during a subsequent scan of the tissue with the apparatus with said imaging planes aligned with said longitudinal axis of said device;
   determining the orientation and position of the device relative to the coordinates of the image slices from the image slices of the subsequent scan; and
   identifying the tip of the device in a final slice from pixel intensity samples obtained along the longitudinal axis of the device.

17. A program storage device readable by a computer, tangibly embodying a program of instructions executable by the computer to perform the method steps for detecting the position and orientation of a tip of an elongated needle-like medical device inserted into tissue of a patient using a scanning apparatus, said method comprising the steps of:
   obtaining a plurality of image slices through the tissue having therein the device during a scan of the tissue using the apparatus with imaging planes aligned with a longitudinal axis of said device;
   determining the orientation and position of the device relative to the coordinates of the image slices from the image slices of the scan by determining eigenvectors and associated eigenvalues of a candidate device in each image slice of the subsequent scan using principle component analysis, and selecting a final slice as the slice with a greatest likelihood of representing the device;
   rotating the final image into a predetermined orientation in the reference coordinate system;
   estimating a reference profile along a center of the device in the rotated final image;
   selecting a reference position along the reference profile;
   calculating a correlation coefficient as a function of pixel intensities sampled at various offsets along the reference profile from the reference position and a pixel intensity sampled at the reference position; and identifying the tip from a smallest offset from the reference position whose correlation coefficient decreases in value and does not increase for increased offsets.

18. The computer readable program storage device of claim 17, before obtaining a plurality of image slices through the tissue having therein the device during a scan of the tissue with the apparatus with imaging planes aligned with a longitudinal axis of said device, the method further comprising:

obtaining a plurality of image slices through the tissue having therein the device during a first scan of the tissue with the scanning apparatus, each image slice having a known orientation with respect to a reference co-ordinate system of the scanning apparatus, the plurality of image slices forming a first image volume;

calculating a feature image from a normalized cross correlation of the slice with a plurality of device templates, each template having a different angular orientation;

thresholding the feature image to obtain a binary image of the device; identifying connected regions in the binary image as candidate device regions; calculating a score for each candidate device region from an area of each region and a ratio of its largest and smallest eigenvalues, and selecting a candidate device region with a highest score as representing the device;

estimating the position and orientation of the device from a center of mass of the selected candidate device region and from the orientation of a largest eigenvector of the candidate device region; and determining an appropriate imaging plane for the scan by referencing the position and angular orientation of the device in each said slice to the reference coordinate system of the scanning apparatus, wherein a longitudinal axis of the device is aligned in an imaging plane of known orientation with respect to the reference coordinate system.

* * * * *